US00PP30289P2

(12) United States Plant Patent
Hansen

(10) Patent No.: US PP30,289 P2
(45) Date of Patent: Mar. 12, 2019

(54) ***PHLOX* PLANT NAMED 'CLOUDBURST'**

(50) Latin Name: ***Phlox* hybrid**
Varietal Denomination: Cloudburst

(71) Applicant: Hans A. Hansen, Zeeland, MI (US)

(72) Inventor: Hans A. Hansen, Zeeland, MI (US)

(73) Assignee: Walters Gardens Inc., Zeeland, MI (US)

( * ) Notice: Subject to any disclaimer, the term of this patent is extended or adjusted under 35 U.S.C. 154(b) by 0 days.

(21) Appl. No.: 15/732,194

(22) Filed: Oct. 2, 2017

(51) Int. Cl.
*A01H 5/02* (2018.01)

(52) U.S. Cl.
USPC ..... Plt./320

(58) Field of Classification Search
USPC ..... Plt./263.1, 320
See application file for complete search history.

(56) References Cited

PUBLICATIONS

Walters Gardens, Inc. Summer 2017-Spring 2018 catalog. https://www.provenwinners.com/sites/provenwinners.com/files/images/professional/catalogs/1-intro-pw_perennials_2018.pdf. retrieved from the internet Oct. 15, 2018. 5 pages. (Year: 2017).*

* cited by examiner

*Primary Examiner* — Susan McCormick Ewoldt
*Assistant Examiner* — Karen M Redden

(57) ABSTRACT

A new and unique cultivar of garden *Phlox* named *Phlox* 'Cloudburst' multi-stemmed, compact, slowly-spreading habit with clean green, glossy, lanceolate leaves with exceptional powdery mildew resistance. Sweetly fragrant flowers of lavender-purple with bright pink eye zones are produced on multiple branched peduncles and cover from the top down to nearly the soil beginning the last week of May and continuing for about five weeks, and repeating through mid-fall. 'Cloudburst' especially suitable as a potted plant, for the garden, for attracting hummingbirds and butterflies, and for cut flower arrangements.

1 Drawing Sheet

Botanical classification: *Phlox* hybrid.
Variety denomination: 'Cloudburst'.

BACKGROUND OF THE INVENTION

The present invention relates to a new and distinct cultivar of *Phlox* plant, known as *Phlox* 'Cloudburst and will be referred to hereafter by its cultivar name or the "new plant". The new plant was the result of a single seedling selection from the cross of *Phlox paniculata* 'Ditomsur' U.S. Plant Pat. No. 21,109 times a proprietary unreleased selection of *Phlox latifolia* (not patented) performed at a wholesale perennial nursery in Zeeland, Mich. on Jul. 14, 2011. The new plant was originally given the breeder code 11-42-1 throughout subsequent evaluations at the same nursery. 'Cloudburst' has been asexually propagated by stem cuttings in the greenhouses at the same nursery in Zeeland, Mich. since 2013. The unique characteristics of the new plant have been found to be reproducible and stable in successive generations of asexually propagated plants and the resultant plants have been found to be identical to the original selection.

No plants of *Phlox* 'Cloudburst' have been sold or disclosed, in this country or anywhere in the world, prior to the filing of this application, with the exception of that which may have been sold or disclosed within one year of the filing date of this application and was either derived directly or indirectly from the inventor.

BRIEF SUMMARY OF THE PLANT

*Phlox* 'Cloudburst' is unique from its parents and all other tall garden *Phlox* or other *Phlox* known to the inventor. The new plant differs from the female parent 'Ditomsur' in that the female parent has red-purple colored flowers later in the season, is slightly taller and has narrower foliage. Compared to the male parent *Phlox latifolia* the new plant has more flatter and fuller flower faces with petals of lavender-purple rather than pinkish. The most closely comparison cultivar known to the inventor is *Phlox* 'Fashionably Early Flamingo' U.S. Plant patent application Ser. No. 15/530,085. Compared with 'Cloudburst', 'Fashionably Early Flamingo' is taller and produces flowers of more lavender pink, habit is more rhizomatous and foliage more glossy. Compared with all of the above cultivars 'Cloudburst' flowering covers nearly the whole mound from top to soil, whereas each of the above cultivars flower more exclusively at the top. 'Cloudburst' differs from all other *Phlox* known to the inventor in the following repeatedly observed traits in combination:

1. Plants of broad, mounding, billowy habit, slowly spreading by short rhizomes, producing clean, glossy, clean green, lanceolate leaves.
2. Showing exceptional powdery mildew resistance.
3. Multiple branched stems produce rounded mounds of flowers starting very early in the season.
4. Sweetly fragrant flowers on strong wiry stems of about 30 cm tall producing sweetly-fragrant, initially lavender-purple flower faces with bright pink eye zones.
5. Flowers cover the plant from the top down to the nearly the soil.
6. Excellent re-blooming through mid-fall.

BRIEF DESCRIPTION OF THE DRAWINGS

The photographs of the new plant demonstrate the unique traits of 'Cloudburst' and the overall appearance of the plant at three-years-old. The colors are as accurate as reasonably possible with color reproductions. Variation in ambient light spectrum, source and direction may cause the appearance of minor variation in color.

DETAILED BOTANICAL DESCRIPTION

Figure 1:
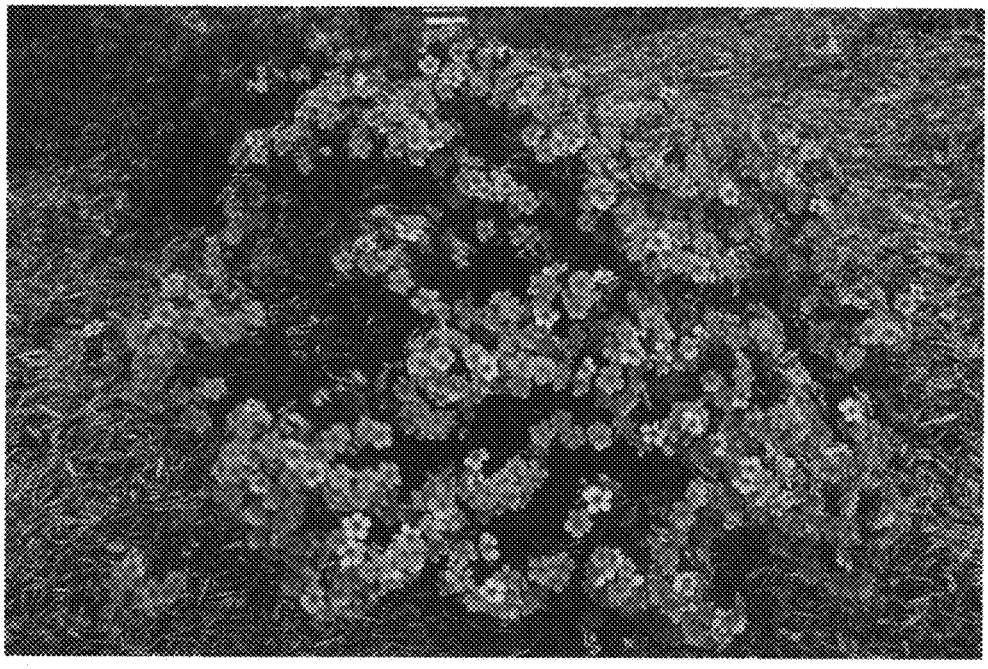
FIG. 1 shows the new plant in peak flower in the landscape.
Figure 2:
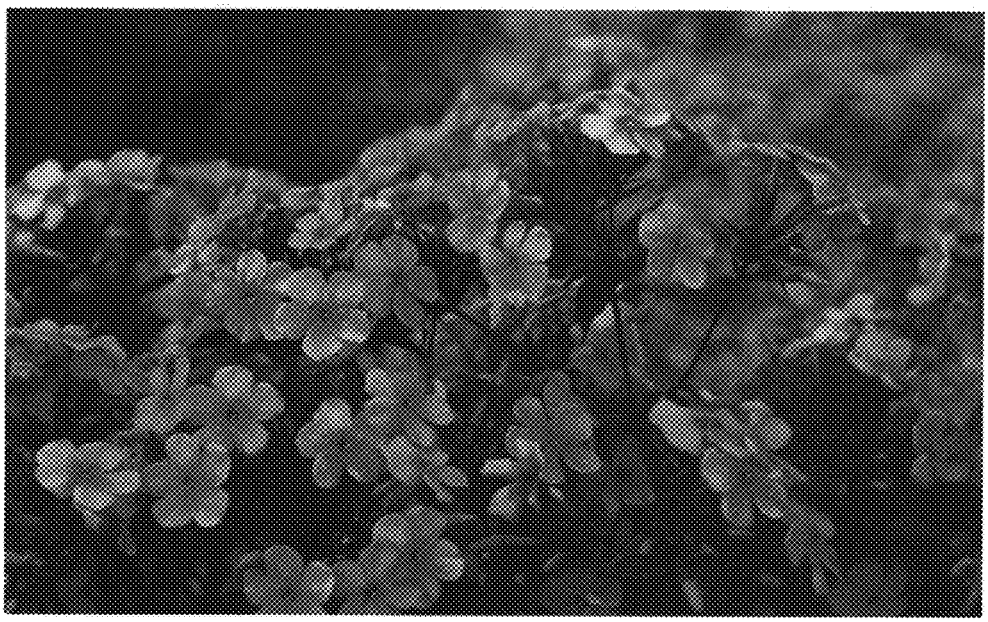
FIG. 2 shows a close-up of the floriferous flower head with flowers and buds.

The following descriptions and color references are based on the 2015 edition of The Royal Horticultural Society Colour Chart except where common dictionary terms are used. *Phlox* 'Cloudburst' has not been observed under all possible environments. The phenotype may vary slightly with different growing environments such as temperature, light, fertility, soil pH, moisture and maturity levels, but without any change in the genotype. The following observations and size descriptions are based on two-year-old plants in the full sun trial garden of a wholesale perennial nursery in Zeeland, Mich. with supplemental fertilizer and water as needed.

Botanical classification: *Phlox* hybrid;

Parentage: Female or seed parent *Phlox paniuclata* 'Ditomsur'; male or pollen parent *Phlox latifolia;*

Plant habit: Hardy herbaceous perennial, densely upright, producing about four rigid upright stems; flowering and about 55.0 cm tall and about 42.0 cm wide; flowering begins about the last week of May in Michigan and continuing for about 5 weeks and repeating through summer and until heavy frost;

Propagation: Stem cuttings; rooting in about 14 days;

Time to produce finished crop in 3.8 liter pots: About 8 to 10 weeks; moderate rate of growth;

Root: Primary roots to about 1.0 mm thick; secondary fibrous and freely branching; color creamy white to tan depending on soil type;

Leaves: Simple, opposite, lanceolate; entire and microciliate margin; acute to acuminate apex; rounded to attenuate base;

Leaf size: To about 115.0 mm long by about 37.0 mm wide, average about 95.0 mm long by about 32.0 mm wide;

Leaf surfaces: Abaxial sparsely puberulent, lustrous; adaxial sparsely puberulent, semi-lustrous;

Leaf color expanding: Abaxial nearest RHS 146B with heavy blush of nearest RHS N186C; adaxial nearest RHS 137D with heavy blush of RHS N186C;

Leaf color at flowering: Abaxial nearest RHS 146B with heavy blush of nearest RHS N186C, adaxial nearest RHS 137A;

Foliage fragrance: None detected;

Veins: Pinnate; glabrous abaxial and adaxial; midrib about 1.0 mm wide at base, slightly sunken adaxial and raised abaxial;

Vein color: Abaxial midrib nearest RHS 145C, adaxial midrib nearest RHS 145C; other adaxial and abaxial veins same color as surrounding leaf;

Petiole: Leaves sessile;

Stems: Terete; stiff; wiry; strong; upright; finely and sparsely puberulent; average about 30.0 cm long and 8.0 mm diameter at base;

Stem color: Between 146B and RHS 146A with blushing of between RHS N187A and RHS 187A;

Nodes: About nine per stem below flowers; average internode length about 4.6 cm;

Node color: Nearest RHS 187A;

Inflorescence: A branched compound corymb of about 250 to 300 flowers; about 21.0 cm long and 19.0 cm across;

Flowers: Perfect; salverform with flat face and long fused tube; actinomophic; typically with five petals; about 3.2 cm long total with tube about 2.0 cm long; face about 3.5 cm across; attitude upright to outward;

Flower longevity: About 5 days on plant or as cut flower; self-cleaning;

Flower fragrance: Faint to lightly sweet;

Buds one to two days prior to opening: Narrowly oblanceolate, to nearly clavate; acute apex with petals twisted about each other; base fused; about 33.0 mm long and 3.0 mm diameter in tube and swollen to 6.0 mm diameter toward apex;

Bud color: Petals and base nearest RHS 83D;

Petals: Five; margin entire; apex rounded; base fused into tube; abaxial and adaxial limb glabrous, abaxial tube surface puberulent, adaxial tube glabrous except pubescent in region about 5.0 mm to 10.0 mm from base;

Petal size: Basal 20.0 mm fused into tube, to a diameter of about 2.0 diameter; limbs about 18.0 mm across, and face about 16.0 mm long; imbricate about 3.0 mm of the petals to either side;

Petal color: Young flowers—Adaxial face between RHS N78B and RHS N78C toward center and nearest RHS N81C toward apex; abaxial limb nearest RHS N80C toward center and nearest RHS N82D toward apex; adaxial tube nearest RHS 145C toward base with pubescence white nearest RHS NN155D and distal 13.0 mm of tube nearest RHS 83D, abaxial tube basal 3.0 mm nearest RHS 145C with distal 17.0 mm between RHS N80B and RHS N80C; Mature flowers—Adaxial face distal and leading petal edges nearest RHS 85D with center and back edges nearest RHS N80D; abaxial limb edges lighter than RHS 85D with remaining portion nearest RHS N87D;

Androecium:

*Filaments*.—Typically five; adnate to adaxial petals except free in terminal 1.0 mm; varying lengths between 18.0 mm and 13.0 mm, less than 0.5 mm in diameter; white, nearest RHS NN155D to nearest RHS 85D.

*Anther*.—Five; oblong elliptic; basifixed; longitudinal; about 4.0 mm long by 1.0 mm wide; color nearest RHS 10A.

*Pollen*.—Abundant; color nearest RHS 11A.

Gynoecium: One pistil per flower; to about 20.0 mm long;

*Style*.—Terete; about 17.0 mm long and less than 0.5 mm diameter when flower is mature; color base nearest RHS 145D, mid-section lighter than RHS 186D or RHS N155B, just below stigma nearest RHS 145D.

*Stigma*.—Trifurcate in the distal 1.5 mm, less than 0.25 mm in diameter; persistent after flower abscission; color nearest RHS 150C.

*Ovary*.—Superior; globose; about 2.5 mm long and 1.5 mm diameter; color nearest RHS 144A.

Calyx: Tubular; to about 16.0 mm long and 4.0 mm wide at apex;

Sepals: Five; lanceolate; narrowly acute apex, margin entire; base fused; surface matte and sparsely puberulent abaxial and sparsely and micro-puberulent and lustrous adaxial;

individually about 16.0 mm long and 1.5 mm wide; fused in basal 6.0 mm forming tube 2.5 mm diameter at base and 4.0 mm diameter at apex;

Sepal color: Abaxial apex nearest RHS 137C with heavy blushing of nearest RHS N186C in intense light with margin transparent to translucent with blushing nearest RHS N186C; adaxial base nearest RHS 145A, longitudinal center nearest RHS 138A margins (about 0.5 mm wide) nearest RHS NN155D to translucent with blushing nearest RHS 187D;

Peduncle: Glabrous, stiff, strong, upright, terete; about 30.0 cm long and 2.5 mm diameter at base of flower branches; branches to about 15.0 cm long and 2.0 mm diameter at base;

Peduncle color: Between RHS 146B and RHS 146A with blushing between RHS N187A and RHS 187A;

Pedicel: Terete; to about 7.0 mm long and 1.0 mm diameter; glabrous to micro-puberulent;

Pedicel color: Nearest RHS 137C with heavy blushing of nearest RHS N186D in intense light;

Fruit: Dehiscent capsule with flat base and acute to mucronate apex; about 7.0 mm long and 5.0 mm diameter; color at maturity nearest RHS 161C;

Seeds: Up to four; slightly flattened ellipsoid; about 3.5 mm long and 2.5 mm across and 2.0 mm thick; color nearest RHS 202A;

Hardiness and culture: The new plant grows best with plenty of moisture and adequate drainage; hardy to at least from USDA zone 4 through 8.

Disease and pest resistance: *Phlox* 'Cloudburst' demonstrated the excellent powdery mildew resistance caused by *Erysiphe cichoracearum* under conditions of intense pressure that would normally show symptoms.

I claim:

1. A new and distinct cultivar of hybrid *Phlox* plant named *Phlox* 'Cloudburst', as herein described and illustrated.

* * * * *